United States Patent
Madjarov

(10) Patent No.: US 8,992,530 B2
(45) Date of Patent: Mar. 31, 2015

(54) METHOD AND SYSTEM FOR LONGITUDINAL CLOSURE OF DISSECTED STERNUMS

(71) Applicant: The Charlotte-Mecklenburg Hospital Authority, Charlotte, NC (US)

(72) Inventor: Jeko Metodiev Madjarov, Charlotte, NC (US)

(73) Assignee: The Charlotte-Mecklenburg Hospital Authority, Charlotte, NC (US)

( * ) Notice: Subject to any disclaimer, the term of this patent is extended or adjusted under 35 U.S.C. 154(b) by 138 days.

(21) Appl. No.: 13/679,095

(22) Filed: Nov. 16, 2012

(65) Prior Publication Data

US 2013/0178906 A1    Jul. 11, 2013

Related U.S. Application Data

(60) Provisional application No. 61/585,025, filed on Jan. 10, 2012.

(51) Int. Cl.
*A61B 17/56* (2006.01)
*A61B 17/58* (2006.01)
(Continued)

(52) U.S. Cl.
CPC ......... *A61B 17/8004* (2013.01); *A61B 17/8076* (2013.01); *A61B 17/8085* (2013.01); *A61B 17/823* (2013.01)
USPC .......................................................... 606/74

(58) Field of Classification Search
USPC .......................................................... 606/74
See application file for complete search history.

(56) References Cited

U.S. PATENT DOCUMENTS

| 4,003,376 A | 1/1977 | McKay et al. |
| 5,139,498 A | 8/1992 | Astudillo Ley |

(Continued)

FOREIGN PATENT DOCUMENTS

| CN | 10-2327145 A | 1/2012 |
| DE | 20 2010 012426 | 11/2010 |

(Continued)

OTHER PUBLICATIONS

Bennett-Guerrero et al.; "Pilot Study of Sterna Plating for Primary Closure of the Sternum in Cardiac Patients" Innovations; 2011; vol. 6; pp. 382-388.

(Continued)

*Primary Examiner* — Andrew Yang
(74) *Attorney, Agent, or Firm* — Alston & Bird LLP

(57) ABSTRACT

Systems, devices, and methods for longitudinal closure of a dissected sternum are provided. The system includes first and second reinforcing members, fasteners, and closure members. Each reinforcing member is configured to be placed on an outer surface of a respective sternum portion, such that each reinforcing member is longitudinally disposed on an opposite side of a sternum opening with respect to the other reinforcing member. Fasteners may be placed in holes defined in the reinforcing members to secure a respective reinforcing member to a corresponding sternum portion. The closure members, which may be sternal closing wires, may then be wrapped around the sternum portions and the reinforcing members transversely to close the sternum opening. The system provides for a low installed profile, enhancing patient comfort and facilitating healing, and also provides for quick and easy access to the thoracic cavity for re-do sternotomies, if needed.

19 Claims, 9 Drawing Sheets

(51) Int. Cl.
*A61B 17/82* (2006.01)
*A61F 2/30* (2006.01)
*A61B 17/80* (2006.01)

(56) References Cited

U.S. PATENT DOCUMENTS

| | | | |
|---|---|---|---|
| 6,338,734 | B1 | 1/2002 | Burke et al. |
| 6,712,821 | B2 | 3/2004 | Gabbay |
| 6,872,210 | B2 | 3/2005 | Hearn |
| 7,651,498 | B2 | 1/2010 | Shifrin et al. |
| 7,704,252 | B2 | 4/2010 | Albertson et al. |
| 8,221,421 | B2 | 7/2012 | Hearn |
| 8,343,155 | B2 * | 1/2013 | Fisher et al. .............. 606/74 |
| 8,425,572 | B2 * | 4/2013 | Grevious .............. 606/280 |
| 2004/0010256 | A1 | 1/2004 | Gabbay |
| 2005/0240198 | A1 | 10/2005 | Albertson et al. |
| 2006/0122611 | A1 | 6/2006 | Morales et al. |
| 2010/0131013 | A1 | 5/2010 | Ralph et al. |
| 2012/0271311 | A1 | 10/2012 | Hearn |
| 2013/0178906 | A1 | 7/2013 | Madjarov |

FOREIGN PATENT DOCUMENTS

| | | |
|---|---|---|
| DE | 202010012426 U1 | 12/2010 |
| DE | 10 2009 038392 A1 | 3/2011 |
| RU | 2391934 C1 | 6/2010 |
| WO | WO 2008/073898 A2 | 6/2008 |
| WO | WO 2013/003719 A1 | 1/2013 |

OTHER PUBLICATIONS

Cicilioni et al.; "Sternal Wound Reconstruction with Transverse Plate Fixation" 2005; Plast. Rescontr. Surg., v. 115; pp. 1297-1303.
Dieselman; Comparison of Alternative Rigid Sterna Fixation Techniques; Thesis; 2011.
Fawzy, et al.; Sternal Plate Fixation for Sterna Wound Reconstruction: Initial Experience (Retrospective Study); 2011; J. Cardiothoracic Surgery; v. 6; pp. 3-7.
Ma, et al.; "Application of the Titanium Plate Fixation System in Sternum Transverse Incisions" 2011; The American Surgeon; v. 77; pp. 1477-1482.
Moerenhout, et al.; Titanium Transverse Plate Fixation: A New Solution for Old Sterna Problems; 2009; Acta Chir. Belg.; v. 109; pp. 371-375.
Raman, et al.; "Sternal Closure with Titanium Plate Fixation—A Paradigm Shift in Preventing Mediastinitis" 2006; Interactive Cardiovascular and Thoracic Surgery; v. 5; pp. 336-339.
Tasolglu & Lafci; Novel Longitudinal Plate-Fixation Technique; 2012; Texas Hart Inst. J.; v. 39; pp. 215-217.
Voss, et al.; Sternal Reconstruction with Titanium Plates in Complicated Sterna Dehiscence; 2008; Eur. J. of Cardiothoracic Surg.; v. 34; pp. 139-145.
Cardio Thoracic and Vascular Surgery; Sternal Talon®—The innovative sternal closure; KLS Martin (undated).
SternaLock® Blu—The new standard in primary closure; Biomet Microfixation; Copyright 2011.
SternaLock® Blu; Primary Closure System; Biomet Microfixation; Copyright 2011, www.biometmicrofixation.com.
Titanium Sternal Fixation System; For Stable Internal Fixation of the Sternum; Synthes CMF; Copyright 2006; 12 pages.
International Search Report for Application No. PCT/US2012/065610; dated Feb. 18, 2013.
Moerenhout et al., "Titanium Transverse Plate Fixation: a New Solution for Old Sternal Problems," *Acta Chirurgica Belgica*, vol. 109, 2009, pp. 371-375.
Voss et al., "Sternal Reconstruction with Titanium Plates in Complicated Sternal Dehiscence," *European Journal of Cardio-Thoracic Surgery*, vol. 34, Issue 1, Jul. 2008, pp. 139-145.
"510(K) Summary: Sternal Plating System," KLS-Martin, L.P., Jun. 20, 2003, 6 pages.
"LSF—Longitudinal Sternal Fixation," Handout from KLS Martin Group, Annual Meeting of the Society of Thoracic Surgery (STS), Jan. 26-30, 2013, Los Angeles, 1 page.
Written Opinion from corresponding International Application No. PCT/US2012/065610, mailed Apr. 10, 2013.
International Preliminary Report on Patentability from corresponding International Application No. PCT/US2012/065610, dated Jul. 15, 2014.
International Search Report and Written opinion for Application No. PCT/US2014/051017 dated Oct. 27, 2014.

* cited by examiner

METHOD AND SYSTEM FOR LONGITUDINAL CLOSURE OF DISSECTED STERNUMS

CROSS-REFERENCE TO RELATED APPLICATIONS

This application claims the benefit of U.S. Provisional Application No. 61/585,025 entitled "Method and System for Longitudinal Closure of Dissected Sternums," filed Jan. 10, 2012, the contents of which are incorporated herein in their entirety.

FIELD OF THE INVENTION

The present invention relates generally to methods and systems for longitudinal closure of dissected sternums. More specifically, methods and apparatuses are described for holding together two portions of a dissected sternum, such as resulting from a sternotomy.

BACKGROUND

The sternum, or breastbone, is a long flat bone in the upper middle of the front of the chest. The sternum actually consists of three separate bones that may partially or completely fuse together: the manubrium (the upper section of the sternum), the corpus or body (the longer middle section of the sternum to which the ribs are joined), and the xiphisternum or xiphoid process (the cartilaginous extension, usually ossified in adults, that forms the bottom section of the sternum).

The sternum, together with the rib cage, serves to protect vital organs such as the heart and lungs from damage. Thus, in cases where access to one of these vital organs is needed, such as for open heart surgery, a longitudinal incision is typically made along a midline of the sternum, and the two resulting portions of the sternum may be forced apart to allow the surgeon to gain access to the patient's thoracic cavity.

Once the procedure is complete, the dissected portions of the sternum must be held together in a closed configuration to allow the bone and tissue to heal. In some cases, however, the sternotomy must be re-done at a later date as a result of a complication from the first surgery or a subsequent issue that arises. Depending on how the sternum was closed, it is sometimes difficult to determine a location for the second incision and/or gain quick access to the thoracic cavity once it has been closed following the first sternotomy.

Accordingly, there is a need for a system and method for longitudinally closing dissected sternums that is safe, reproducible, simple to administer, causes the least amount of pain to the patient, and provides for easy re-entry to the thoracic cavity in the event a second procedure is necessary.

BRIEF SUMMARY OF EXAMPLE EMBODIMENTS

Accordingly, embodiments of a system and method are described that can provide for longitudinal closure of a dissected sternum. The sternum may, for example, comprise first and second sternum portions separated by a sternum opening. In particular, embodiments of a system for longitudinal closure of a dissected sternum may include first and second reinforcing members, a plurality of fasteners, and a plurality of closure members. Each reinforcing member may be configured to be placed on an outer surface of a respective sternum portion such that each reinforcing member is longitudinally disposed on an opposite side of the sternum opening with respect to the other reinforcing member. Each reinforcing member may define a plurality of holes. Each hole of the first and second reinforcing members may be configured to receive one of the fasteners so as to secure a respective reinforcing member to a corresponding sternum portion, and the outer surface of each reinforcing member may define at least one concavity configured to receive a respective closure member. The plurality of closure members may be configured to hold together the first and second sternum portions such that the sternum opening is in a substantially closed position.

In some cases, each reinforcing member may be configured to be installed such that a lateral edge of the respective reinforcing member is substantially aligned with a lateral edge of a corresponding sternum portion. A lateral edge of each respective reinforcing member may comprise a bevel configured to contact a corresponding portion of a closure member applied thereto. Additionally or alternatively, a lateral edge of each respective reinforcing member may comprise at least one recess disposed between adjacent holes of the respective reinforcing member.

A lateral edge of each respective reinforcing member may comprise at least one engaging feature configured to engage a corresponding portion of a closure member applied thereto. Additionally or alternatively, a lateral edge of each respective reinforcing member may define a curvature substantially corresponding to a curvature of a lateral edge of the corresponding sternum portion. Each reinforcing member may, in some cases, be configured to extend from a manubrium of the corresponding sternum portion to a xiphoid process of the corresponding sternum portion.

In other embodiments, a reinforcing member for longitudinal closure of a dissected sternum is described. The reinforcing member may be configured to be placed on an outer surface of a sternum portion such that the reinforcing member is longitudinally disposed proximate a lateral edge of the sternum portion. The reinforcing member may comprise a plurality of holes, at least one concavity defined in an outer surface of the reinforcing member between adjacent holes, and a bevel defined in at least a lateral edge of the reinforcing member. Each hole may be configured to receive a fastener so as to secure the reinforcing member to the sternum portion, and the at least one concavity may be configured to receive a closure member. The bevel may be configured to contact a corresponding portion of a closure member applied thereto.

The lateral edge of the reinforcing member may comprise at least one recess disposed between adjacent holes of the reinforcing member. Furthermore, the lateral edge of the reinforcing member may comprise at least one engaging feature that is configured to engage a corresponding portion of the closure member applied thereto. Additionally or alternatively, the lateral edge of the reinforcing member may define a curvature substantially corresponding to a curvature of the lateral edge of the sternum portion. For example, the reinforcing member may define a proximal end, and the curvature of the lateral edge of the reinforcing member may comprise an angle of approximately 5° to approximately 10° defined between the proximal end and a midline of the reinforcing member.

In some cases, an inner surface of the reinforcing member may define at least one concavity configured to engage an outer surface of the sternum portion. The reinforcing member may define a thickness that varies along the length of the reinforcing member. The reinforcing member may comprise pre-defined lines of weakness configured to allow adjustment of a length of the reinforcing member.

In still other embodiments, a method for longitudinal closure of a dissected sternum is described. According to the method, a first reinforcing member is attached to an outer surface of the first sternum portion, and a second reinforcing member is attached to an outer surface of the second sternum portion, such that each reinforcing member is longitudinally disposed on an opposite side of the sternum opening with respect to the other reinforcing member. A plurality of closure members may be wrapped around the first and second sternum portions so as to close the sternum opening by extending each closure member around a first lateral edge of the first sternum portion, behind the first and second sternum portions, and around a second lateral edge of the second sternum portion such that the closure member is disposed in concavities defined in an outer surface of the first and second reinforcing members. Furthermore, the ends of each closure member may be secured together to maintain the sternum opening in a substantially closed position. In some embodiments, a lateral edge of the first reinforcing member may be substantially aligned with a lateral edge of the first sternum portion and a lateral edge of the second reinforcing member may be substantially aligned with a lateral edge of the second sternum portion.

In some cases, a length of at least one of the first and second reinforcing members may be adjusted, such as via pre-defined lines of weakness defined in the reinforcing members. At least one of the first and second reinforcing members may be bent such that a curvature of the at least one of the first and second reinforcing members substantially corresponds to a curvature of the outer surface of a respective one of the first and second sternum portions. The steps of attaching the first and second reinforcing members may, in some cases, comprise attaching the first and second reinforcing members such that a proximal end of each of the first and second reinforcing members is disposed on a manubrium of the corresponding sternum portion and a distal end of each of the first and second reinforcing members is disposed proximate a xiphoid process of the corresponding sternum portion.

BRIEF DESCRIPTION OF THE DRAWINGS

Figure 1:
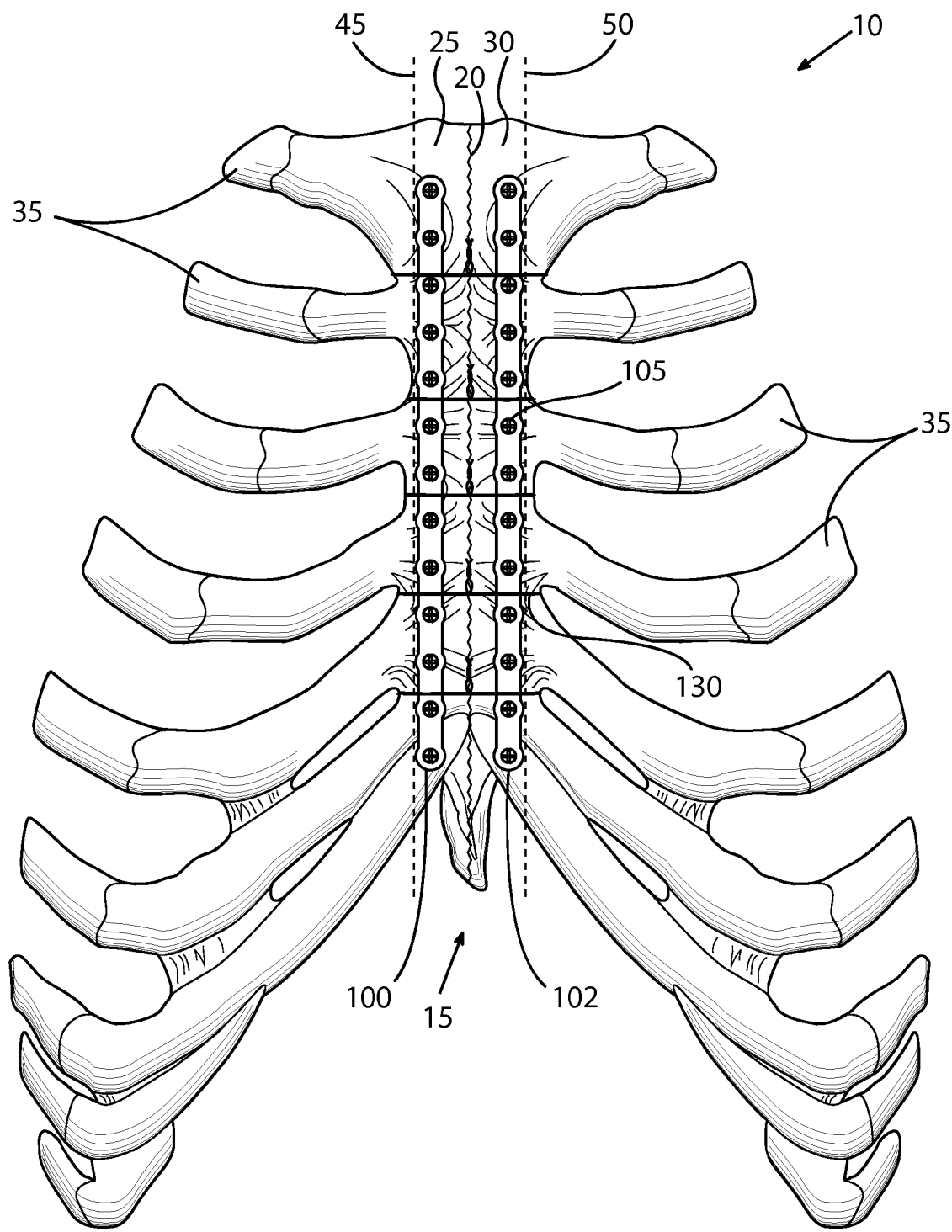
Figure 2A:
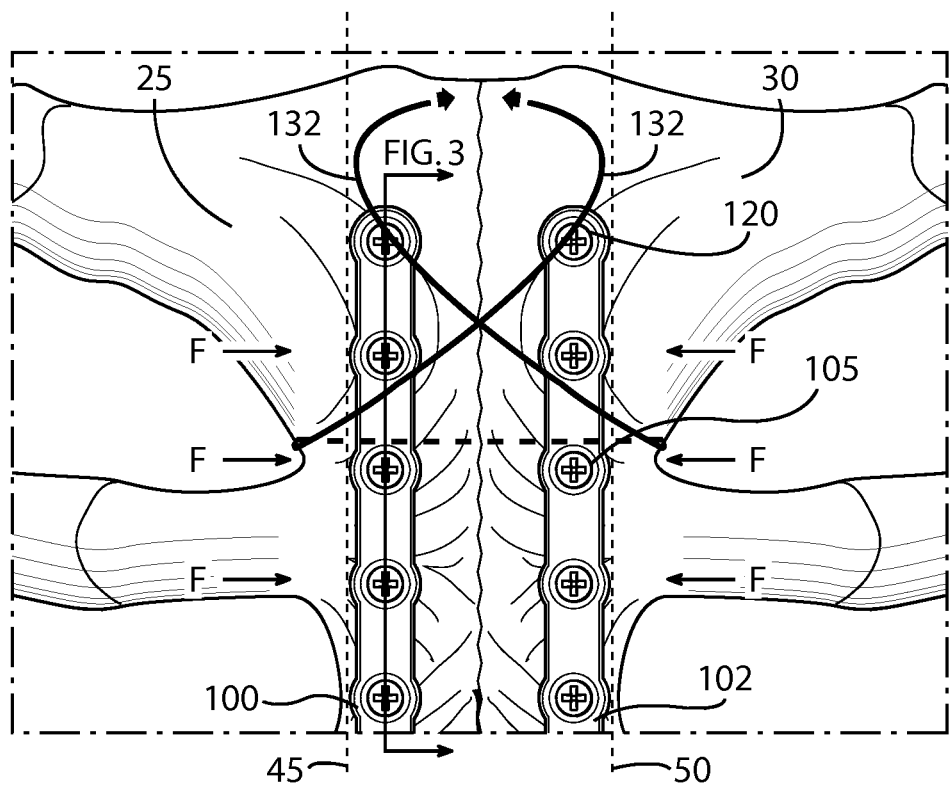
Figure 2B:
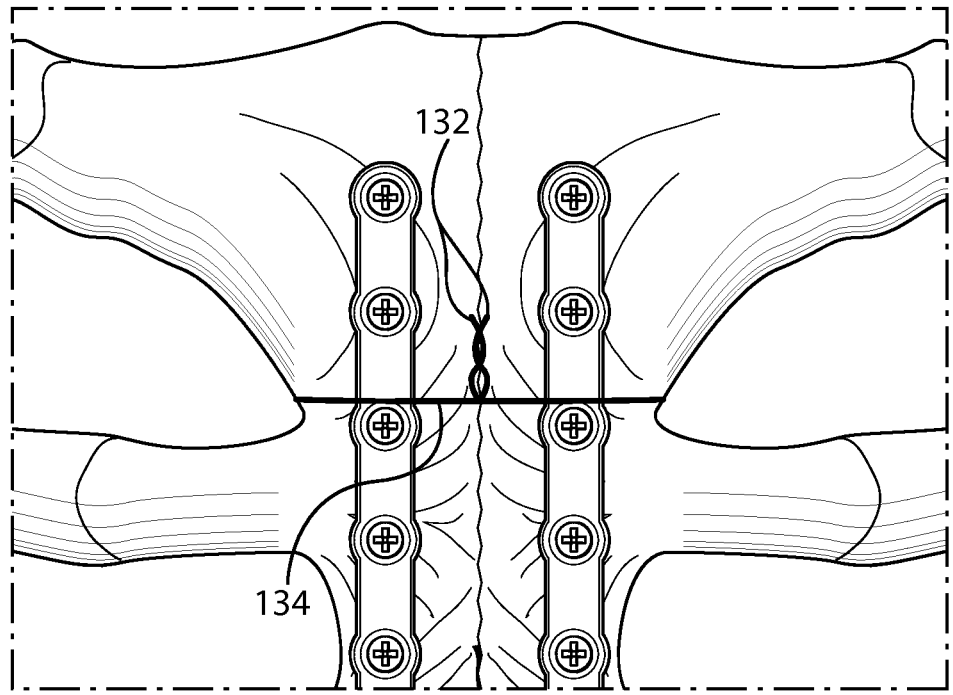
Figure 3:
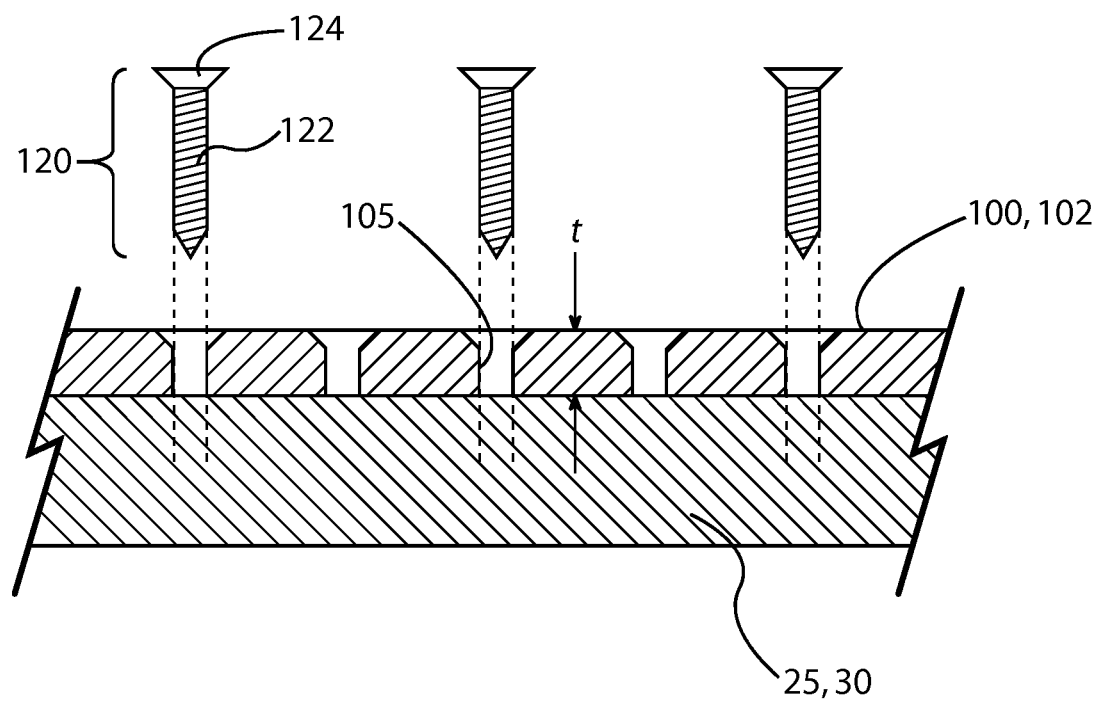
Figure 4:
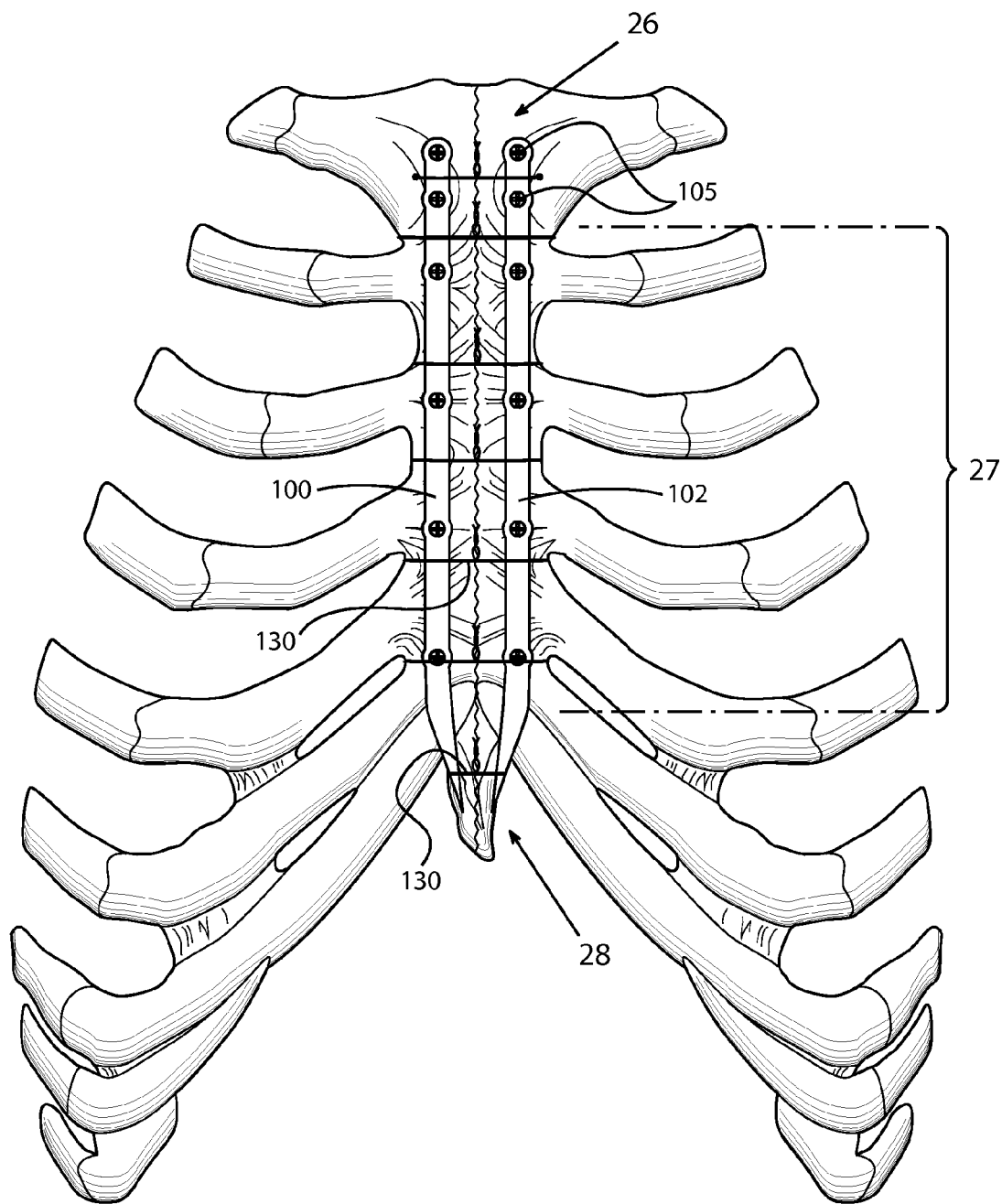
Figure 5:
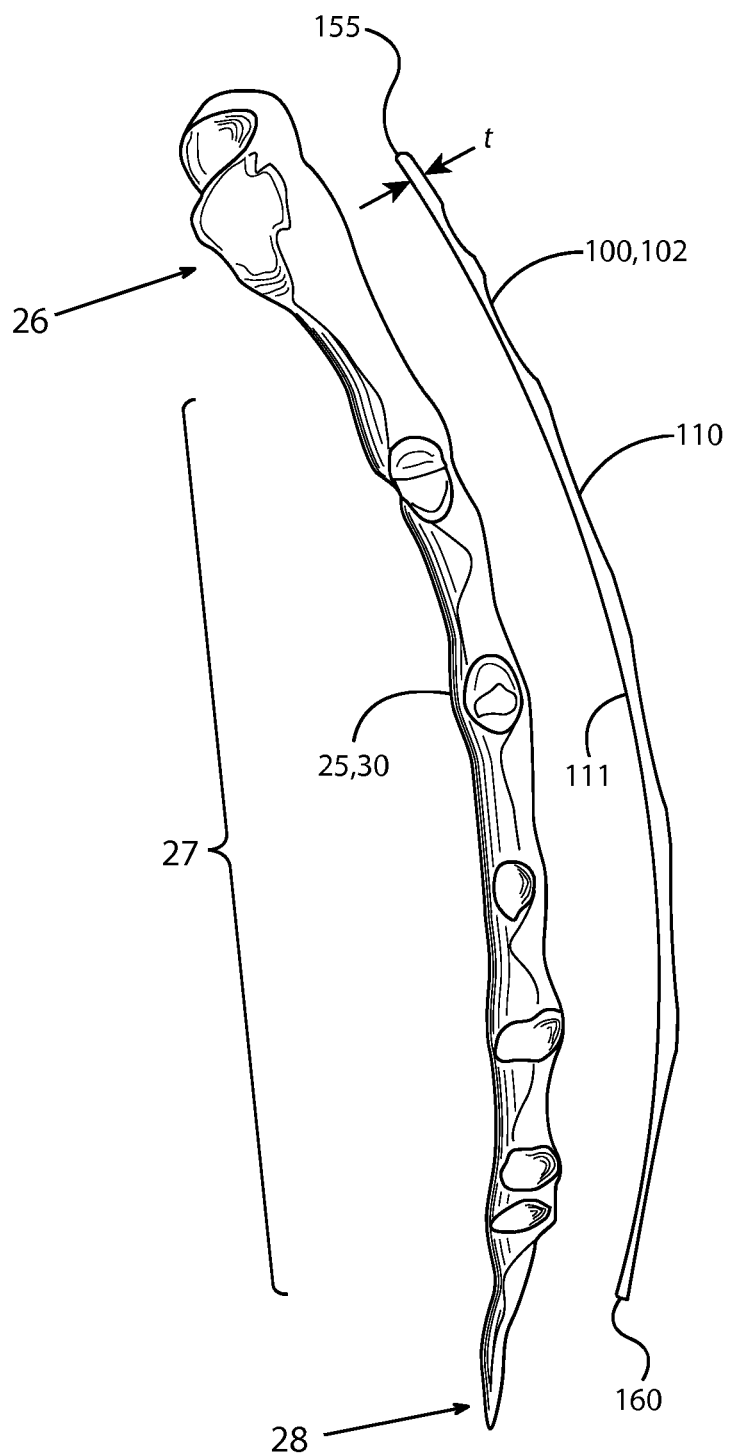
Figure 6:
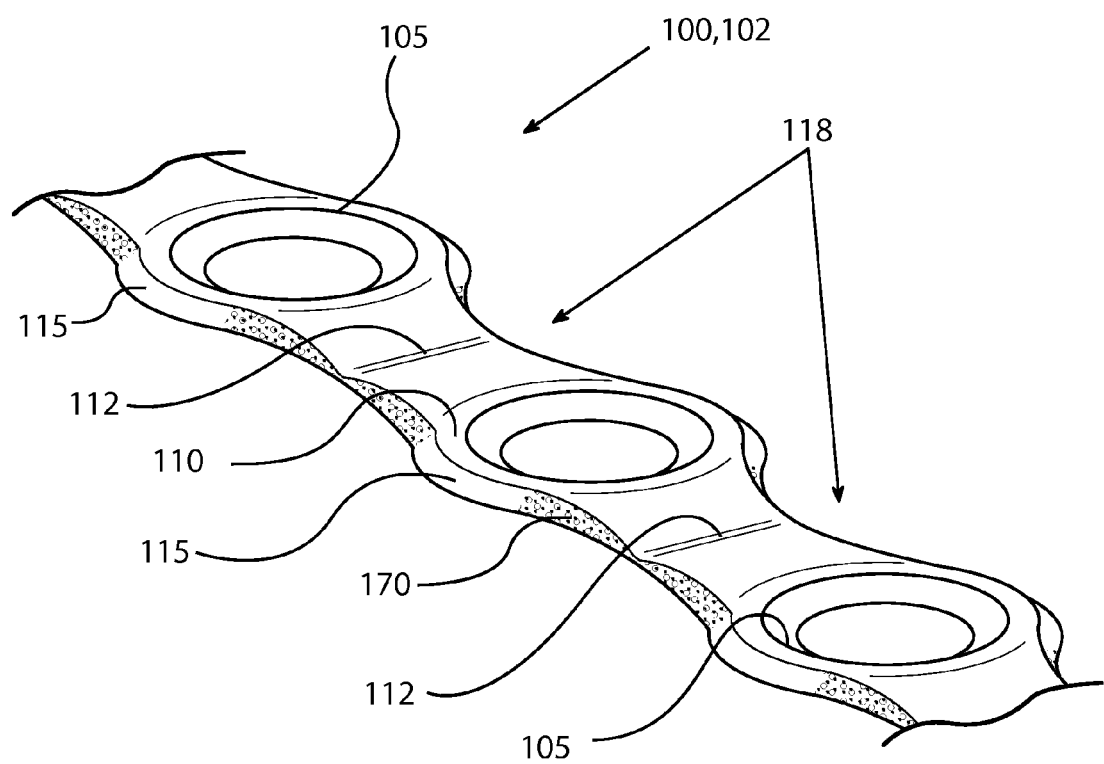
Figure 7:
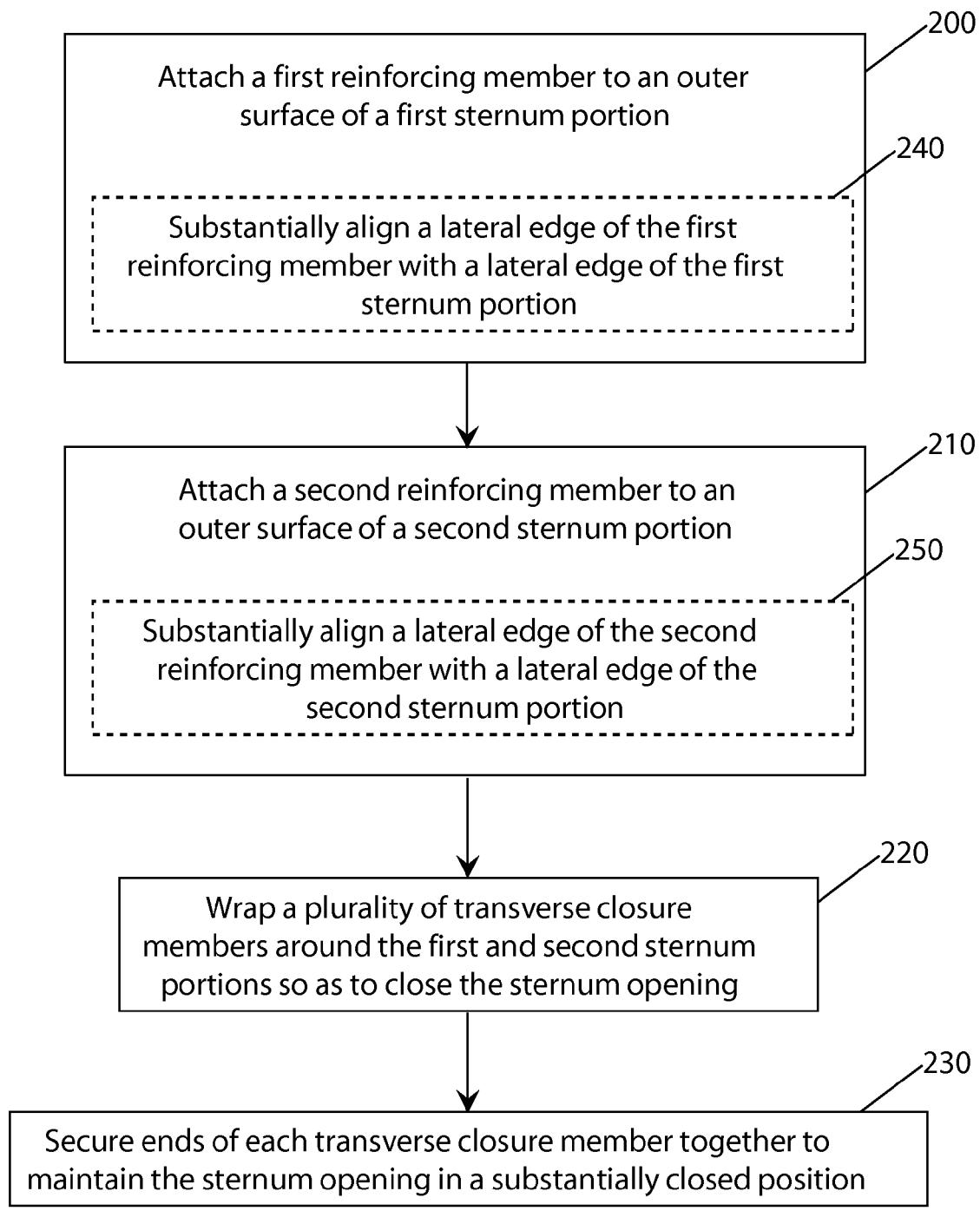
Figure 8:
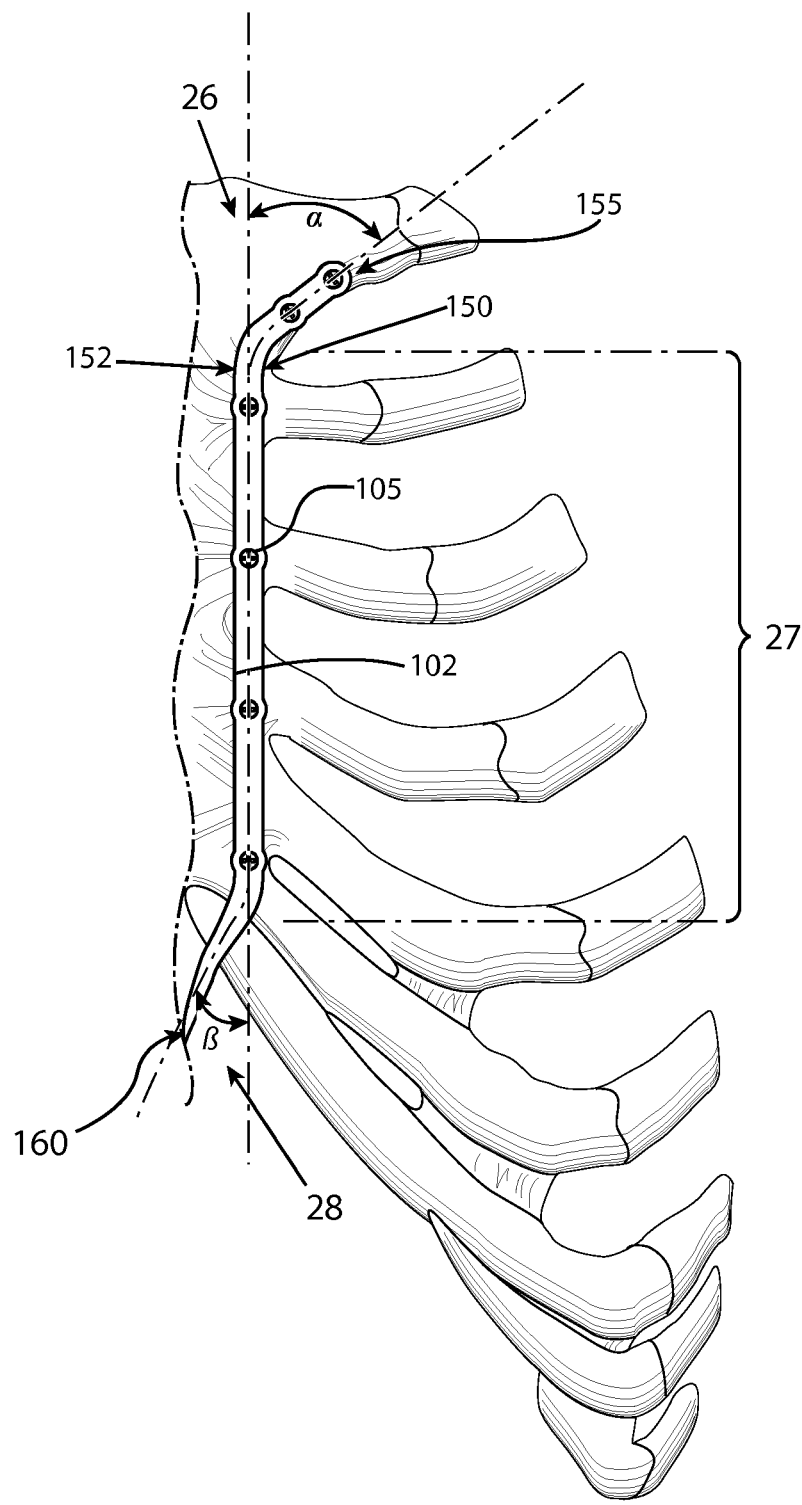
Figure 9:
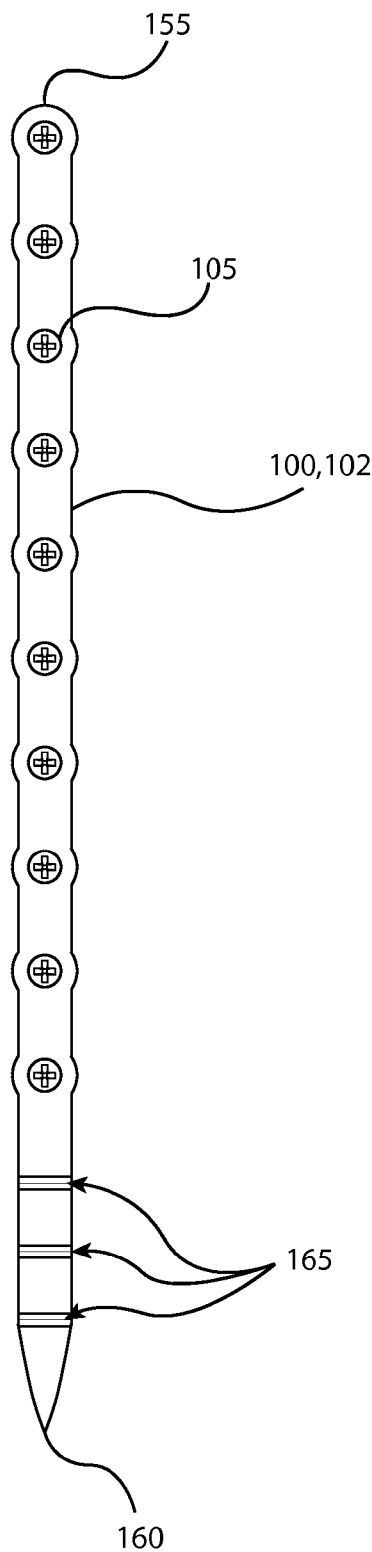

Having thus described the invention in general terms, reference will now be made to the accompanying drawings, which are not necessarily drawn to scale, and wherein:

FIG. 1 shows a schematic representation of a system for longitudinal closure of a dissected sternum in accordance with an exemplary embodiment of the present invention;

FIGS. 2A and 2B illustrate a close-up view of the closure of a sternum using reinforcing members and a closure member in accordance with an exemplary embodiment of the present invention;

FIG. 3 shows a partial cross-section of one of the reinforcing members of FIG. 2A in accordance with an exemplary embodiment of the present;

FIG. 4 shows a schematic representation of a system for longitudinal closure of a dissected sternum in accordance with another exemplary embodiment of the present invention;

FIG. 5 shows a side view of the sternum and the reinforcing members in accordance with an exemplary embodiment of the present invention;

FIG. 6 shows a close-up perspective view of a portion of a reinforcing member illustrating a bevel, concavities, recesses, and engaging features in accordance with an exemplary embodiment of the present invention;

FIG. 7 illustrates a flowchart of a method for longitudinally closing a dissected sternum in accordance with an exemplary embodiment of the present invention;

FIG. 8 shows a schematic representation of a system for longitudinal closure of a dissected sternum in accordance with another exemplary embodiment of the present invention; and FIG. 9 shows a schematic representation of a reinforcing member with pre-defined lines of weakness in accordance with another exemplary embodiment of the present invention.

DETAILED DESCRIPTION

Some embodiments of the present invention will now be described more fully hereinafter with reference to the accompanying drawings, in which some, but not all, embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout.

As used herein, the terms "lateral" and "laterally" refer to a location of an anatomical structure (such as a bone) or movement in a direction toward a point that is farthest from the center of the respective structure. Similarly, the terms "medial" and "medially" refer to a location or movement toward a point closest to the center of the respective structure. Furthermore, although each example described herein refers to the closure of a dissected sternum, embodiments of the described invention may be used to hold together other bones in which a longitudinal fracture or cut is made.

Referring now to FIG. 1, a schematic representation of a system 10 for longitudinal closure of a dissected sternum 15 is shown. The dissected sternum 15 may be, for example, the sternum of a human patient in which a longitudinal incision 20 has been made to create a first sternum portion 25 and a second sternum portion 30. In this regard, each sternum portion 25, 30 may articulate several ribs 35. The first and second sternum portions 25, 30 may thus be separated by a sternum opening 40 (shown in FIG. 2A), via which a surgeon making the incision 20 may access the thoracic cavity and anatomical structures, such as the heart, that are located therein. For example, during open heart surgery, a two- to five-inch incision may be made in the chest, and the sternum (or at least an upper part of the sternum) may be cut, as noted above. The two sternum portions 25, 30 (which may, in some cases, be connected at their lower ends if the cut is only in the upper part of the sternum) may be pulled away from each other and held in an open position to enlarge the sternum opening 40 and allow the surgeon to perform a procedure (such as a bypass or a valve repair) on the heart or neighboring structures. Once the procedure is complete, the first and second sternum portions 25, 30 may be brought back together and fixed in a closed position so that the bone of the sternum and the surrounding tissue can heal.

Traditionally, sternal closing wires have been used to suture two sternum portions together. Using this conventional method, the sternal closing wires are passed around the two sternum portions, and the ends of the wires are twisted together proximate the location of the sternal incision to hold the sternum portions toward each other and close the sternum opening. Because the sternal closing wires are disposed directly on the bone of the sternum portions, there is often a risk that forces applied to the sternum, such as longitudinal shear, transverse shear, and lateral distraction forces resulting from the patient's movement in performing everyday tasks, will cause the wire to cut into the bone in the various locations where the wires contact the bone. This may, at best, cause the patient to suffer from pain and discomfort and, at worst, cause serious damage to the sternum, such as additional fractures of the sternum where the wires have cut all the way through the bone.

Other types of closure devices have also been used in some cases to repair sternums after a sternotomy, including devices that require transverse fixation. Such devices may include two pieces, each piece having curved prongs located on the lateral end for gripping the lateral edge of a corresponding sternum portion and an interlocking medial end. Once each piece has been installed on a respective sternum portion, the two sternum portions may be brought together such that the medial interlocking end of each of the pieces may be joined to hold the sternum portions together. Several of the devices may be installed along the length of the sternum, with corresponding pieces being interlocked when the sternum portions are brought together.

Such transverse fixation devices may come in various sizes to enable proper securement to sternums of different sizes and configurations. To effect proper closure of the sternum opening, it is typically vital for the surgeon to perform accurate measurements before the closure procedure to select the appropriate size of device for each location along the sternum at which the device will be used. Accurate measurements may also be important during the closure procedure to ensure that the corresponding interlocking pieces are installed at the correct locations to enable them to be aligned for interlocking when the sternum portions are brought together.

Although properly installed transverse fixation devices of the type described above may provide a solid closure of the sternum opening, such devices are not recommended for certain patients having a high risk of requiring subsequent sternotomies, such as those prone to infection, because of the difficulty associated with removing the installed devices to regain access to the thoracic cavity. In particular, these types of interlocking transverse fixation devices necessarily cross the midline of the sternum (e.g., in the area of the sternum opening) and tend to present an obstacle to a surgeon performing a subsequent procedure requiring access to the sternum. The surgeon must therefore physically remove the transverse fixation device to be able to perform the subsequent sternotomy. In some cases, the patient's body may incorporate the device into the bone as the sternum heals. In these cases, subsequent procedures typically require a surgeon to cut the device out of the patient's bone tissue, which may cause bleeding and/or weaken the bone.

Referring back to FIG. 1, a system 10 for longitudinal closure of a dissected sternum is provided that includes first and second reinforcing members 100, 102, fasteners 120 (shown in FIG. 3), and closure members 130. The closure members 130 may, for example, be sternal closing wires as described above or cables. Referring to FIG. 2A, each reinforcing member 100, 102 is configured to be placed on an outer surface of a respective sternum portion 25, 30, such that each reinforcing member is longitudinally disposed on an opposite side of the sternum opening 40 with respect to the other reinforcing member. A number of holes 105 may be defined in each reinforcing member 100, 102, with each hole configured to receive one of the fasteners 120 so as to secure a respective reinforcing member to a corresponding sternum portion 25, 30, as shown in FIG. 3. The fasteners 120 may be, for example, bone screws that have a shaft portion 122 and a head portion 124. The bone screws may range from about 8 mm to 14 mm long to properly engage the sternum portion without creating a risk of puncture of any organs or tissue located behind the sternum. The shaft portion 122 may be sized to have an outer diameter substantially equal to or slightly larger than the diameter of the hole 105, such that the fastener forms a tight fit with the reinforcing member 100, 102. In this regard, the bone of the respective sternum portion 25 may be pre-drilled in some cases to receive the fastener 120. In other cases, however, insertion of the fastener 120 through the hole 105 and into the underlying bone may serve to secure the fastener to the bone of the respective sternum portion 25, 30 without pre-drilling. The holes 105 in some embodiments may be counterbored, as shown, such that the head portion 124 of the fastener 120 is substantially flush with the outer surface of the reinforcing member 100, 102 or recessed within the reinforcing member.

In some embodiments, the number of holes 105 provided in each reinforcing member 100, 102 may be greater than the number of holes needed to effect securement of the respective reinforcing member to the corresponding sternum portion 25, 30. For example, although holes 105 may be provided approximately every 2 cm along a length of each reinforcing member 100, 102, the surgeon may choose to install a fastener 120 in every second or third hole 105, leaving some of the holes empty. In other cases, the surgeon may decide to install two or three fasteners 120 in an upper part of each reinforcing member 100, 102 (e.g., corresponding to the manubrium of the sternum) and two or three fasteners in a lower part of the reinforcing member (e.g., corresponding to the body of the sternum). The location of the fasteners 120 with respect to each reinforcing member 100, 102 may be based on the surgeon's preferences, the condition of the bone (e.g., bone density or other defects in the bone), the condition of surrounding tissue, and/or other factors.

In some cases, reinforcing members 100, 102 may be provided having fewer holes 105 (e.g., holes spaced farther apart or disposed in locations where the surgeon is more likely to require holes for applying the fasteners 120). For example, the holes 105 may be arranged as shown in FIG. 4, with two holes spaced about 1 cm apart in an upper section of the reinforcing member 100, 102 for attachment to the manubrium of the sternum and four holes spaced farther apart (e.g., spaced about 3 cm apart) in the remainder of the reinforcing member for attachment to the body portion of the sternum. As such, two closure members 130 may be applied to the reinforcing members 100, 102 in the area of the manubrium 26 as shown, with one or more of the closure members going through the bone. Four to five additional closure members 130 may be applied to the reinforcing members 100, 102 over the rest of the sternum, in some cases including the xiphoid process 28. In other configurations, not shown, three holes spaced about 1 cm apart may be provided in the upper section of the reinforcing member 100, 102 and four to six holes spaced about 2 cm to about 3 cm apart may be provided in the remainder of the reinforcing member, with different numbers of closure members 130 used as needed.

By providing fewer holes, an overall thickness t (FIG. 3) of the reinforcing members 100, 102 may be decreased, allowing for a thinner reinforcing member to be used having the same strength. For example, whereas a reinforcing member 100, 102 having evenly-spaced holes 105 about 2 cm apart may be required to have a thickness t of between approximately 1 mm to approximately 3 mm, a reinforcing member with evenly-spaced holes about 3 cm apart may only require a thickness of approximately 0.75 mm to approximately 1.25 mm to achieve a comparable strength. Thinner reinforcing members 100, 102 may allow the reinforcing members to have greater pliability or flexibility, such that the reinforcing members may be able to better conform to the curvature of the surface of the sternum portion to which the respective reinforcing member is fastened. In addition, thinner reinforcing members 100, 102 may also provide for a lower profile of the installed reinforcing members and closure members, thereby minimizing the protrusion of the reinforcing members and closure members out from the sternum and reducing pain and discomfort to the patient, as described below.

In this regard, in some cases, the reinforcing members 100, 102 may be pre-bent, as shown in FIG. 5, such that the curvature of the reinforcing members corresponds to the curvature of the surface of the sternum portions 25, 30. The reinforcing members 100, 102 may be pre-bent as part of the manufacturing process, such that the surgeon would receive the reinforcing members already bent, or the reinforcing members may be configured such that the surgeon may be able to bend the reinforcing members manually prior to attaching the reinforcing members to the respective sternum portions. As a result of the curvature of the reinforcing members 100, 102, when the reinforcing members are attached to the respective sternum portions 25, 30 via the fasteners 120, there may be a greater area of contact between the surface of the reinforcing members and the adjacent surface of the sternum portions. Better contact, in turn, may result in fewer localized forces and less stress on the reinforcement members and the areas of the bone surrounding the fasteners 120, as the reinforcing members will have a lesser tendency to pull the fasteners out of the bone as compared to reinforcing members that are not curved.

Turning again to FIG. 2A, once the reinforcing members 100, 102 have been positioned along each sternum portion 25, 30 and held in place via the fasteners 120, closure members 130 may be applied at various locations along the sternum to hold the dissected sternum portions 25, 30 together and close the sternum opening 40. In this regard, each closure member 130 may have two ends 132, and one of the ends may be passed behind the two sternum portions (shown in dashed lines in FIG. 2A). In some embodiments, the ends may be accessible to the surgeon such that once the sternum opening 40 has been sufficiently closed (e.g., through application of a force F in the direction of the arrows), the wire ends 132 of each closure member 130 may be twisted together to form a loop 134 for holding the sternum portions against each other, as depicted in FIG. 2B. In this regard, as shown in FIGS. 1 and 2B, the closure members 130 may be configured to extend between adjacent ribs 35 from a first lateral edge 45 of the first sternum portion 25 to a second lateral edge 50 of the second sternum portion 30 so as to span the sternum opening such that the first and second sternum portions 25, 30 may be held together, maintaining the sternum opening in a substantially closed position.

Again, the surgeon may apply any number of the closure members 130 to the reinforcing members 100, 102 as necessary to provide an adequate closing force to the sternum portions. For example, as shown in FIG. 1, a closure member 130 may be provided between each pair of adjacent ribs 35. In other examples, multiple closure members 130 may be applied in close proximity to extend the line of the approximation, providing better support of the closure and potentially preventing dehiscence, as shown in FIG. 4. For example, in FIG. 4, a closure member 130 may be applied near the cartilaginous portion of the xiphoid process 28 (the lowermost part of the sternum), which may be particularly useful in the case of a patient having a relatively short sternum. Thus, in some embodiments, one or both reinforcing members 100, 102 may be configured to extend longitudinally from the manubrium 26 of the sternum, down the length of the body 27 of the sternum, to the xiphoid process 28 of the sternum.

In some embodiments, the thickness t of the reinforcing members 100, 102 may vary over a length of the respective reinforcing member. For example, with reference to FIGS. 5 and 6, the thickness t may increase gradually in the vicinity of each hole 105 to strengthen those regions where there is less material due to the holes and may decrease in the areas between adjacent holes.

With reference to FIG. 6, for example, in some embodiments, the outer surface 110 of each reinforcing member 100, 102 may define at least one concavity 112 configured to receive a respective closure member 130. The reinforcing member 100, 102 may, for example, have longitudinally spaced holes 105 with concavities 112 longitudinally spaced between adjacent holes. In one embodiment, the concavity 112 may be, for example, a dip or recess that extends substantially between adjacent holes 105 with a gradual curvature, whereas in another embodiment the concavity may be a groove or channel with steeper sidewalls. Regardless, the concavity 112 may have a maximum depth that accommodates, for example, between half of the diameter of the closure member 130 and the full diameter of the closure member. Thus, the concavity may have a maximum depth that is between approximately 15% to approximately 50% of the nominal thickness of the reinforcing member in some embodiments. For example, in one embodiment, the reinforcing member 100, 102 may have a concavity 112 with a depth of approximately 0.25 mm, such that the reinforcing member may have a thickness that varies along the length of the reinforcing member between 0.75 mm to 1 mm in the case of a reinforcing member with a nominal thickness of 1 mm and between approximately 1 mm and 1.25 mm in the case of a reinforcing member with a nominal thickness of 1.25 mm. An inner surface 111 of the reinforcing member 100, 102 (shown in FIG. 5) may also define concavities in some cases that may allow the inner surface of the reinforcing member to more closely correspond to and better engage the outer surface of the corresponding sternum portion.

In addition to providing a visual indication to the surgeon as to where the closure members 130 are to be applied, the concavities 112 may also limit movement of the closure member 130 with respect to the reinforcing member 100, 102 during and after placement of the closure members 130 within the concavities and may allow for a lower profile of the installed reinforcing members and closure members. As a result, in some embodiments, the presence of the concavity may minimize the protrusion of the reinforcing members and closure members out from the sternum, especially for thinner patients, which may help to reduce pain experienced by patients during the recovery process.

The first and second reinforcing members 100, 102 may be configured to have additional features for facilitating their installation and use with the fasteners 120 and/or closure members 130. For example, continuing to refer to FIG. 6, in some embodiments at least a lateral edge of each reinforcing member 100, 102 (e.g., an edge 150 of the reinforcing member disposed closest to the first or second lateral edge of the sternum shown in FIG. 8 when installed) may comprise a non-perpendicular surface 115, such as a bevel, chamfer, or rounded edge, collectively referred to herein as a "bevel" or "beveled surface" for ease of explanation. The bevel 115 may be configured to contact a corresponding portion of a closure member 130 that is applied thereto. The beveled surface 115 may provide for more gradual receipt of the closure member 130 as the closure member is wrapped around the lateral edge of the respective sternum portions. As a result, the force applied by the closure member against the lateral edge of the reinforcing member (and, as a result, the respective first or second lateral edge of the sternum 45, 50) may be reduced. In addition, any lateral protrusion of the closure member 130 as it wraps around the reinforcing member may be minimized, further minimizing the profile of the device.

Additionally or alternatively, the first and second reinforcing members 100, 102 may be configured such that at least the lateral edge of each respective reinforcing member comprises at least one recess 118 disposed between adjacent holes of the respective reinforcing member, as shown in FIG. 6. For example, each reinforcing member 100, 102 may measure between approximately 4 mm to approximately 8 mm at the widest parts (e.g., surrounding the holes 105) and may narrow to between approximately 3 mm to approximately 6 mm at the recesses 118.

In cases where the reinforcing members 100, 102 include both recesses 118 and concavities 112, described above, each concavity may be formed in the area of the recessed portion of the reinforcing member, as shown. In this way, the closure member 130 may be received by both the recess 118 (as illustrated in FIG. 1) and the concavity 112. Moreover, an area of the beveled surface 115 corresponding to the location of the concavity 112 may include an engaging feature 170, shown in FIG. 6, which may comprise knurls, channels, or other texturing of the beveled surface configured to enhance the engagement of the bevel with the closure member 130, such as by increasing the friction between the two and thereby maximizing the tendency of the closure member to stay in the location the engaging feature.

In some embodiments, each reinforcing member 100, 102 may be substantially symmetrical about its respective longitudinal axis. For example, both longitudinal edges of the reinforcing member (lateral edge 150 and medial edge 152, shown in FIG. 8) may be beveled and/or both longitudinal edges may comprise recesses and/or engaging features, and the longitudinal edges may have substantially the same shape. As a result, the surgeon may be able to install the reinforcing members 100, 102 without regard to which member is placed on the first sternum portion and which is placed on the second sternum portion or the orientation of each with respect to the sternum portion it is placed on. In other cases, however, the medial edge 152 may not include a bevel 115 or an engaging feature 170 as described above with reference to FIG. 6, and/or at least the lateral edge 150 may define a curvature that corresponds to the curvature of the lateral edge of the sternum portions 25, 30, as shown in FIG. 8.

In this regard, with reference to FIG. 8, the reinforcing member 100, 102 may define a proximal end 155 (i.e., an end that is disposed closest to the patient's head when installed) and a distal end 160 (i.e., an end that is disposed farthest from the patient's head when installed). The proximal end 155 may define an angle α with a midline M of the main body of the reinforcing member 100, 102 (i.e., the portion of the reinforcing member extending between the proximal and distal ends, which may be relatively straight). The angle α may be, for example, approximately 5° to approximately 10°, such as between approximately 5° and approximately 7°. Similarly, the distal end 160 may define an angle β with a midline M of the main body of the reinforcing member 100, 102, and the angle β may be, for example, approximately 5° to approximately 10°, such as between approximately 5° and approximately 7°. In some cases, the angle β may be defined such that the distal end 160 is on an opposite side of the midline M, as shown, whereas in other cases the angle β may be defined such that the distal end is on the same side of the midline M, depending on the configuration of the patient's anatomy and the patient's condition. The curvature of the reinforcing members 100, 102 may allow the reinforcing members to be installed as close as possible to the lateral edge of the respective sternum portion, such that the closure members 130 are supported by the reinforcing members as the closure members are wrapped around the sternum portion, rather than being supported by and in direct contact with the bone. In this way, the tendency of the closure members to dig into and damage the bone may be reduced.

The reinforcing members 100, 102 may each have a length that is sized to accommodate any size of sternum. In this regard, the reinforcing members 100, 102 may have a length, such as approximately 25 cm to approximately 30 cm, that can accommodate a taller patient with a longer sternum, while at the same time can be cut by the surgeon into a shorter reinforcing member 100, 102 to accommodate a patient with a shorter sternum. For example, as shown in FIG. 9, in some embodiments, the distal end 160 may define one or more lines of weakness 165 configured such that the surgeon may cut or break the material of the reinforcing member along the predefined line of weakness. The line of weakness 165 may, for example, be formed mechanically, such as via etchings, grooves, or perforations defined in the material, or may be a result of the choice of material in the region of the line of weakness, such as due to the use of a different material in such areas. The reinforcing members 100, 102 may be made of any biocompatible materials, such as, for example, Nitinol, titanium, stainless steel, biomaterials, or polymer materials including biodegradable materials. Such materials may also be used for the fasteners 130.

In some embodiments, the reinforcing members 100, 102 may be made of more than one material. For example, a lateral edge of each reinforcing member 100, 102 may be made of metal, such as stainless steel, whereas the remainder of the reinforcing member may be made of a polymer configured to biodegrade (e.g., dissolve) in the patient's body after a certain amount of time. The fasteners 120, in this case, may also be made of the biodegradable polymer. In such a case, the biodegradable portions of the installed system may dissolve as the patient's sternum heals, and the metal lateral edge of the reinforcing member 100, 102, for example, may be incorporated into the patient's bone with the passage of time. If a subsequent procedure is required, the surgeon may be able to perform an additional sternotomy by cutting through any closure members 130 that may remain in place to dissect the sternum and then using the already incorporated metal of the lateral edges of the previously installed system as the reinforcement for new closure members to be installed. Thus, in addition to providing a visual guide for the location of the subsequent dissection, the surgeon is not required to install additional reinforcing members to effect the subsequent closures. This may be particularly beneficial in pediatric cases of congenital defects or adult congenital defects, where multiple procedures may be required as the patient's body grows.

Having described the components of the system and their interaction with each other and the patient's sternum, a method of longitudinally closing a dissected sternum comprising first and second sternum portions separated by a sternum opening will now be described with regard to FIG. 7. Initially, a first reinforcing member may be attached to an outer surface of the first sternum portion, and a second reinforcing member may be attached to an outer surface of the other sternum portion, such that each reinforcing member is longitudinally disposed on an opposite side of the sternum opening with respect to the other reinforcing member at Blocks 200, 210. The reinforcing members may be attached, for example via fasteners, as described above with respect to FIG. 3. Thereafter, a plurality of closure members may be wrapped around the first and second sternum portions so as to close the sternum opening by extending each closure member around a first lateral edge of the first sternum portion, behind the first and second sternum portions, and around a second lateral edge of the second sternum portion such that the closure members are disposed in concavities and/or grooves defined in an outer surface of the first and second reinforcing members. Block 220. The ends of each closure member may then be secured together to maintain the sternum opening in a substantially closed position at Block 230.

In some cases, each reinforcing member may be configured to be installed such that a lateral edge of the respective reinforcing member is substantially aligned with a lateral edge of a corresponding sternum portion, as illustrated in FIG. 8. For example, each reinforcing member 100, 102 may be attached to a respective sternum portion 25, 30 such that the distance between the lateral edge of the reinforcing member (e.g., at its most laterally-disposed part, such as in the portion in which a hole 105 is defined) and the corresponding lateral edge of the sternum portion to which it is fastened is minimized, given the natural curvature of the lateral edge of the respective sternum portions. Thus, the steps of attaching the first and second reinforcing members may include substantially aligning a lateral edge of the first reinforcing member with a lateral edge of the first sternum portion and substantially aligning a lateral edge of the second reinforcing member with a lateral edge of the second sternum portion. FIG. 7, Blocks 240, 250. Moreover, the first and second reinforcing members may be attached such that a proximal end of the reinforcing members is disposed on the manubrium of the sternum and the distal end of the reinforcing members is disposed on or near the xiphoid process.

As described above, the length of the reinforcing members may be adjustable. Accordingly, a length of each reinforcing member may be adjustable to accommodate the length of the sternum on which the reinforcing member is applied. Such adjustments may be made, for example, by removing excess portions of the reinforcing members proximate the distal ends, such as by cutting or breaking the reinforcing members along pre-defined lines of weakness as noted above.

The method depicted in FIG. 7 and described above represents only one method of closing a dissected sternum using reinforcing members. The particular method of attachment of the reinforcing member and closure of the sternum will depend on the patient's anatomy, the condition and size of the sternum, the overall medical condition of the patient, the preferences of the practitioner, and other considerations. Optional steps are shown in FIG. 7 using dashed lines.

In comparison to sternal closing wires without reinforcing members, the Inventor believes that the use of sternal closing wires with reinforcing plates as described above provides for increases in the maximum load force that can be supported by the bones in the region of the sternum. For example, when the application of force on a sutured sternum in various loading scenarios was modeled in a testing laboratory, the use of reinforcing members resulted in the sternal closing wires cutting into the bone to a much lesser extent than the scenario without the reinforcing members for a longitudinal applied force, a transverse applied force, and a lateral applied force. In most cases, it was observed that the primary failure mode when reinforcing members were used was the breakage of the ribs themselves, rather than the cutting of the bone by the sternal closing wires. This was particularly true in the case of a lateral applied force (e.g., force applied in the direction from the medial edges of the sternum portions to the lateral edges of the sternum portions).

In summary, embodiments of the invention described herein may allow for simpler, more reliable closure of the sternum for patients having a wide variety of medical conditions, including patients with a high risk of requiring a second sternotomy. For example, the configuration and placement of the reinforcing members 100, 102 described above and, e.g., shown in FIG. 1, significantly reduces the risk of sternal dehiscence by providing a barrier between the closure members and the surface of the bone. In addition, the simple structure of the reinforcing members (e.g., no interlocking parts) provides for a system that is easy to use regardless of the particular shape, folio., or bone quality of the patient's sternum. Thus, a surgeon may be able to use embodiments of the system described herein to treat osteoporotic bones, pectus, and sternal fractures, as well as to perform off-midline sternotomies. Moreover, the reinforcing members may be used to extend the line of approximation (e.g., by applying fasteners to the reinforcing members in the area of the body portion of the sternum and allowing the reinforcing members to extend into the xiphoid process for providing reinforcement for the application of closure members in that area, as described above), thereby providing better support of the closure and potentially preventing dehiscence in cases such as when the patient has a particularly short sternum.

The Inventor believes that embodiments of the present invention may provide for improved splinting of the sternum with possible less pain and greater ease and speed of the patient's recovery. For example, in the case of osteoporotic bone, installation of the described system may allow for less bleeding by approximating the anterior and posterior plates of the sternum in some embodiments. In addition, the reinforcing members may provide the surgeon with a "handle" for manipulating the respective sternum portions to allow for better alignment of the two portions (e.g., to make the portions flush with each other), again resulting in minimized pain and a faster recovery for the patient. The configuration of the reinforcing members may also provide a system that, once installed, has a lower profile than other types of closure devices, which may be especially helpful in the case of thinner patients and/or patients with osteoporetic or weaker bones.

The use of two substantially linear reinforcing members may also facilitate a surgeon's subsequent access to the thoracic cavity by providing a visual indication of the centerline of the sternum (e.g., the centerline being disposed approximately between the medial edges of the two reinforcing members). In the case of a re-do sternotomy, the reinforcing members may be left attached to the respective sternum portions, and the closure members need only be cut through to allow the surgeon access to the sternum for applying a subsequent incision. During the re-do sternotomy, the surgeon may use the reinforcing members as a reinforcement for a medial area of the sternum portions before manipulating the chest (e.g., spreading or lifting the chest, such as through the use of retractors). Following the re-do sternotomy, new closure members may be applied to the previously installed reinforcing members to once again close the sternum opening, as described above. In this regard, the reinforcing members may be used by the surgeon as "handles" to stabilize both sternum portions and to prevent possible fractures. Accordingly, it is believed that using the systems and methods described above, quick and easy access to the thoracic cavity may be available, and the sternum may be closed to allow patient healing to recommence as quickly as possible.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A reinforcing member for longitudinal closure of a dissected sternum, the reinforcing member configured to be placed on an outer surface of a sternum portion such that the reinforcing member is longitudinally disposed proximate a lateral edge of the sternum portion, the reinforcing member comprising:
   a plurality of holes, each hole configured to receive a fastener so as to secure the reinforcing member to the sternum portion;
   at least one pre-defined line of weakness configured to allow adjustment of a length of the reinforcing member; and
   a bevel defined in at least a lateral edge of the reinforcing member that is configured to contact a corresponding portion of a closure member applied thereto.

2. The reinforcing member of claim 1, wherein the lateral edge of the reinforcing member comprises at least one recess disposed between adjacent holes of the reinforcing member.

3. The reinforcing member of claim 1, wherein the lateral edge of the reinforcing member comprises at least one engaging feature configured to engage a corresponding portion of the closure member applied thereto.

4. The reinforcing member of claim 1, wherein the lateral edge of the reinforcing member defines a curvature substantially corresponding to a curvature of the lateral edge of the sternum portion.

5. The reinforcing member of claim 4, wherein the reinforcing member defines a proximal end, and wherein the curvature of the lateral edge of the reinforcing member comprises an angle of approximately 5° to approximately 10° defined between the proximal end and a midline of the reinforcing member.

6. The reinforcing member of claim 1, wherein an inner surface of the reinforcing member defines at least one concavity configured to engage an outer surface of the sternum portion.

7. The reinforcing member of claim 1, wherein the reinforcing member defines a thickness that varies along the length of the reinforcing member.

8. The reinforcing member of claim 1 further comprising at least one concavity defined in an outer surface of the reinforcing member between adjacent holes and configured to receive a closure member.

9. A system for longitudinal closure of a dissected sternum, wherein the dissected sternum comprises first and second sternum portions separated by a sternum opening, the system comprising:
   first and second reinforcing members, each reinforcing member configured to be placed on an outer surface of a respective sternum portion such that each reinforcing member is longitudinally disposed on an opposite side of the sternum opening with respect to the other reinforcing member, wherein each reinforcing member defines a plurality of holes;
   a plurality of fasteners, wherein each hole of the first and second reinforcing members is configured to receive one of the fasteners so as to secure a respective reinforcing member to a corresponding sternum portion; and
   a plurality of closure members, each closure member configured to extend between adjacent ribs from a first lateral edge of the first sternum portion to a second lateral edge of the second sternum portion so as to span the sternum opening,
   wherein a lateral edge of each respective reinforcing member comprises a bevel configured to contact a corresponding portion of a closure member applied thereto, and
   wherein the plurality of closure members is configured to hold together the first and second sternum portions such that the sternum opening is in a substantially closed position.

10. The system of claim 9, wherein each reinforcing member is configured to be installed such that a lateral edge of the respective reinforcing member is substantially aligned with a lateral edge of a corresponding sternum portion.

11. The system of claim 9, wherein a lateral edge of each respective reinforcing member comprises at least one recess disposed between adjacent holes of the respective reinforcing member.

12. The system of claim 9, wherein a lateral edge of each respective reinforcing member comprises at least one engaging feature configured to engage a corresponding portion of a closure member applied thereto.

13. The system of claim 9, wherein a lateral edge of each respective reinforcing member defines a curvature substantially corresponding to a curvature of a lateral edge of the corresponding sternum portion.

14. The system of claim 9, wherein each reinforcing member is configured to extend from a manubrium of the corresponding sternum portion to a xiphoid process of the corresponding sternum portion.

15. A method of longitudinally closing a dissected sternum, wherein the dissected sternum comprises first and second sternum portions separated by a sternum opening, the method comprising:
   attaching a first reinforcing member to an outer surface of the first sternum portion;
   attaching a second reinforcing member to an outer surface of the second sternum portion, such that each reinforcing member is longitudinally disposed on an opposite side of the sternum opening with respect to the other reinforcing member;
   wrapping a plurality of closure members around the first and second sternum portions so as to close the sternum opening by extending each closure member around a first lateral edge of the first sternum portion, behind the first and second sternum portions, and around a second lateral edge of the second sternum portion such that the closure member is disposed in concavities defined in an outer surface of the first and second reinforcing members; and
   securing ends of each closure member together to maintain the sternum opening in a substantially closed position.

16. The method of claim 15, wherein the steps of attaching the first and second reinforcing members comprise substantially aligning a lateral edge of the first reinforcing member with a lateral edge of the first sternum portion and substantially aligning a lateral edge of the second reinforcing member with a lateral edge of the second sternum portion.

17. The method of claim 15 further comprising adjusting a length of at least one of the first and second reinforcing members.

18. The method of claim 15 further comprising bending at least one of the first and second reinforcing members such that a curvature of the at least one of the first and second reinforcing members substantially corresponds to a curvature of the outer surface of a respective one of the first and second sternum portions.

19. The method of claim 15, wherein the steps of attaching the first and second reinforcing members comprise attaching the first and second reinforcing members such that a proximal end of each of the first and second reinforcing members is disposed on a manubrium of the corresponding sternum portion and a distal end of each of the first and second reinforcing members is disposed proximate a xiphoid process of the corresponding sternum portion.

* * * * *